(12) United States Patent
Schütz et al.

(10) Patent No.: US 8,501,056 B2
(45) Date of Patent: Aug. 6, 2013

(54) HOMOGENIZED PRODUCT FOR IMPLANTS AND MICROPARTICLES

(75) Inventors: Gregor Schütz, Holzkirchen (DE); Brigitte Freudensprung, Holzkirchen (DE)

(73) Assignee: Hexal AG, Holzkirchen (DE)

( * ) Notice: Subject to any disclaimer, the term of this patent is extended or adjusted under 35 U.S.C. 154(b) by 1120 days.

(21) Appl. No.: 10/479,114

(22) PCT Filed: May 23, 2002

(86) PCT No.: PCT/EP02/05680
§ 371 (c)(1),
(2), (4) Date: May 3, 2004

(87) PCT Pub. No.: WO02/094226
PCT Pub. Date: Nov. 28, 2002

(65) Prior Publication Data
US 2004/0173923 A1  Sep. 9, 2004

(30) Foreign Application Priority Data

May 23, 2001 (DE) .................................. 101 25 509
Feb. 27, 2002 (DE) .................................. 102 08 382

(51) Int. Cl.
*B05B 3/00* (2006.01)

(52) U.S. Cl.
USPC ................ 264/28; 264/15; 366/144; 514/248

(58) Field of Classification Search
USPC .................. 264/28, 140–145, 239–241, 157, 264/345, 109, 117, 148, 638; 366/342; 425/200–202; 523/200, 105; D24/216
See application file for complete search history.

(56) References Cited

U.S. PATENT DOCUMENTS

| | | | |
|---|---|---|---|
| 3,992,350 A * | 11/1976 | Bensa et al. ................... | 523/309 |
| 4,016,345 A | 4/1977 | Holmes | |
| 4,917,834 A * | 4/1990 | Hadermann et al. .............. | 264/8 |
| 4,978,575 A * | 12/1990 | Ziess ............... | 428/402 |
| 5,134,122 A | 7/1992 | Orsolini ......................... | 514/15 |
| 5,439,688 A * | 8/1995 | Orsolini et al. ............. | 424/489 |
| 5,843,347 A * | 12/1998 | Nguyen et al. ..................... | 264/9 |
| 5,945,128 A | 8/1999 | Deghenghi | |
| 6,077,523 A | 6/2000 | Deghenghi | |
| 6,159,490 A | 12/2000 | Deghenghi | |
| 6,284,269 B1 * | 9/2001 | Struengmann et al. ....... | 424/461 |
| 6,299,639 B1 * | 10/2001 | Castro et al. ................ | 623/1.47 |
| 6,455,526 B1 * | 9/2002 | Kohn et al. ................... | 514/248 |
| 6,712,850 B2 * | 3/2004 | Vyakarnam et al. ........ | 623/15.12 |
| 2003/0031701 A1 * | 2/2003 | Burke ............................ | 424/427 |
| 2004/0254266 A1 * | 12/2004 | Motier et al. .................. | 523/175 |

FOREIGN PATENT DOCUMENTS

| | | |
|---|---|---|
| EP | 0 778 304 B1 | 6/1997 |
| EP | 778 304 A2 | 6/1997 |
| EP | 778 304 A3 | 6/1997 |
| EP | 1 392 248 B2 | 8/2007 |
| FR | 2 418 067 | 9/1979 |
| FR | 2418067 | 9/1979 |
| WO | WO 94/23698 | 10/1994 |
| WO | WO-98/09613 | 3/1998 |
| WO | WO 98/09613 | 3/1998 |
| WO | WO-00/35423 | 6/2000 |
| WO | WO 00/35423 | 6/2000 |
| WO | WO 00/66087 | 11/2000 |

OTHER PUBLICATIONS

International Search Report in PCT/EP02/05680 dated Sep. 20, 2002.
International Preliminary Examination Report in PCT/EP02/05680 dated Sep. 5, 2003.
Opposition filed against the European Patent EP 1 392 248, dated May 7, 2008.
Aulton, The Design and Manufacture of Medicines. *Aulton's Pharmaceutics* Churchill Livingston Elsevier, Third Edition (2007).
K.H. Bauer, K.H. Frömming, C. Führer, Pharmazeutische Technologie, Thieme Verlag 1989, p. 77.
W. Vauck, Grundoperationen chemischer Verfahrenstechnik, Verlag Chemie 1982, pp. 337-338.
Römpp Chemie Lexikon, 9th edition 1990, p. 2149.
Product catalogue from C3-Analysentechnik GmbH, catalogue and price list for sample preparation products and Spex CertiPrep sample preparation, May 2000, p. 6.
User manual for SPEX CertiPrep 6800 Freezer/Mill, 1998.
Summons to oral proceedings in opposition of EP 1 392 248-B2, dated Jul. 31, 2009 (9 pages).
In re Klein, 647 F.3d 1343 (Fed. Cir 2011).
*U.S. Surgical Corp.* v. *Hospital Prods. Int'l Pty. Ltd.*, 701 F. Supp. 314 (D. Conn. 1988).
Perry et al., "Perry's Chemical Engineers' Handbook Seventh Edition", p. 20-31 (1997).
Wise, "Handbook of Pharmaceutical Controlled Release Technology", p. 747 (2000).

* cited by examiner

*Primary Examiner* — Monica Huson
(74) *Attorney, Agent, or Firm* — Jason D. Voight

(57) ABSTRACT

The invention relates to a method for the solvent-free preparation of a homogenizate, especially for implants or microparticles, wherein
  one or more polymers and
  one or more active constituents,
as raw materials, are homogenized together below the glass transition temperature of the polymer(s) and, when homogenization is complete, brought to room temperature.

21 Claims, No Drawings

HOMOGENIZED PRODUCT FOR IMPLANTS AND MICROPARTICLES

This is the U.S. national phase of International Application No. PCT/EP02/05680 filed May 23, 2002, the entire disclosure of which is incorporated herein by reference.

The invention relates to a method for the solvent-free homogenisation of polymers and active constituents, by cold-grinding with the aid of a cryogenic mill, for the manufacture of implants and/or microparticles.

In the case of implant manufacture, according to the state of the art the polymer is first of all dissolved in an organic solvent (for example dichloromethane) and then mixed with an aqueous or organic solution (for example a methanolic solution) of the active constituent. After mixing together for a prolonged period, the solvents are slowly evaporated off at elevated temperature, leaving a homogenised mixture of a polymer and an active constituent, which mixture is further processed to form an implant.

In the case of microparticle manufacture, the active constituent or an aqueous solution thereof is suspended, dispersed or emulsified in an organic solution of the polymer. Spray-drying is then preferably carried out, that is to say, the active ingredient/polymer suspension is atomised in a stream of air and dried. In that manner a homogenised mixture of polymer and active constituent in the form of microparticles is obtained.

The following disadvantages may be observed with that conventional method of homogenisation:

- A large number of active constituents are heat-unstable, that is to say, they decompose at higher temperatures. Since elevated temperatures are necessary for evaporation of the solvents, there is a risk that the content of active constituents will be reduced, with the associated increase in impurities as a result of decomposition products.
- As a rule, proteins can be incorporated in the polymer only with difficulty, using the customary "solvent-extraction-evaporation" technique, since the biological activity of those proteins is frequently appreciably reduced by the use of organic solvents.
- Since organic solvents are used for the homogenisation and cannot be completely removed in the evaporation procedure, impurities occur with increased frequency, and the compatibility is in many cases less good.
- Pollution of the environment by solvent waste is very considerable.
- This method of homogenisation is very time-intensive and lengthy.

Also known, from FR 2 918 067, is the incorporation into polymers, at room temperature, of additives that have been subjected to prior comminution by cryogenic techniques. That prior art does not, however, relate to homogenisates for implants and microparticles. The prior art relevant in that respect is listed in the following Table.

Manufacture of Implants and Microparticles

| Priority year | Preparation in the presence of organic solvents | Preparation in the presence of water | Preparation by melting |
|---|---|---|---|
| 1969 | DE 2 051 580 column 13 "A" and column 14 "C"; column 12, line 14 | | DE 2 051 580 column 14 "B"; column 12, line 14 |
| 1981 | EPO 058 481 | | |
| 1996 | page 11, line 44; page 14, line 3 | WO 98/09 613 page 9, line 12 | |
| 1997 | WO 99/20 253 page 21, claim 1; page 24, claim 22 | | |
| 1998 | W099/38 535 page 24, line 16, page 25, line 26, page 11, line 23 WO 00/33 809 page 5, line 16, page 13, line 5 WO 00/40 259 page 4, lines 20/24; page 11, claim 4 | WO 99/48 517 page 4, line 30, page 8, line 14, page 7, line 12 WO 00/33 809 loc. cit. | |
| 1999 | WO 00/66 087 page 28, claim 1 WO 00/76 483 page 26, claim 1 | | |

The problem of the invention is to develop, for implant and/or microparticle manufacture, a method of homogenisation that manages without organic or aqueous solvents and is free of the above-mentioned disadvantages.

According to one embodiment, the problem underlying the invention is solved by a method for the solvent-free preparation of a homogenisate for implants and/or microparticles wherein one or more polymers and
one or more active constituents, as raw materials, are homogenised together below the glass transition temperature of the polymer(s) and, when homogenisation is complete, brought to room temperature and the homogenisate is obtained.

The raw materials can be used in the form of powders or granules.

The raw materials can be cooled together to a temperature below the glass transition temperature of the polymer(s) and subsequently homogenised.

In the method according to the invention, cooling to a temperature applied in cryogenic technology can be carried out, especially to the temperature of dry ice or of a liquid gas, especially to the temperature of liquid nitrogen.

Also, in the method according to the invention, cooling to the working temperature of a cryogenic mill can be carried out.

In the method according to the invention, the two process steps of cooling and homogenisation can be carried out repeatedly in succession.

Homogenisation can be carried out mechanically, especially by grinding. In particular, grinding can be carried out with the aid of a cryogenic mill.

In addition, the homogenisate obtained in the method according to the invention can be further processed to form an implant. For such further processing, reference can be made, for example, to the prior art mentioned at the outset, for example to WO 98/09 613.

The homogenisate obtained in the method according to the invention can also be extruded, and divided into portions to form implant(s). For that too, reference can be made, for example, to the prior art mentioned at the outset, for example to WO 98/09 613.

In addition, the homogenisate according to the invention can be further processed to form microparticles. The homogenisate according to the invention can be further processed to form microparticles by means of extrusion and subsequent grinding.

For example, the homogenisate according to the invention can be further processed to form microparticles by comminuting the extrudate obtained into smaller units, prior to the grinding procedure.

Also, an extrudate that has been obtained from a homogenisate of the invention can be ground to form microparticles at a temperature lying below the glass transition temperature of the polymer(s).

The grinding can be carried out at a temperature applied in cryogenic technology, especially at the temperature of dry ice or of a liquid gas, especially at the temperature of liquid nitrogen.

The microparticles can be produced especially by grinding the implant(s) in a cryogenic mill.

According to a further embodiment, the invention relates to a homogenisate for implants that is obtainable by the method according to the invention.

According to a further embodiment, the invention relates finally to an implant obtainable by the method according to the invention.

According to a further embodiment, the invention relates finally to microparticles obtainable by the method according to the invention. Microparticles as such are known from the prior art listed above, for example WO 00/66 087.

It has therefore been possible to solve the problem according to the invention by homogenising the polymer(s), suitable for an implant or for microparticles, and at least one active constituent in a cryogenic mill (Freezer Mill) without solvent. Examples of cryogenic mills may be found in Obenauf et al. in SPEX CertiPrep Handbook of Sample Preparation and Handling, SPEX CertiPrep Inc., Metuchen (N.J.), USA, 1999. With this method, an increase in temperature and the application of a vacuum is not necessary. The homogenisate exhibits a very high degree of homogenisation, with the result that the surface of an implant according to the invention is smooth and homogeneous.

The homogenisation method according to the invention can include the following steps:
(a) weighing out the polymer(s) and at least one active constituent
b) transferring the raw materials into the grinding drum of the cryogenic mill
c) pre-cooling the raw-material mixture using liquid nitrogen
d) homogenisation, by alternating periods of grinding and cooling
e) thawing the ground material to room temperature.

The grinding drum of the cryogenic mill can be made of polycarbonate or high-quality alloy steel. A freely moving grinding rod (pestle), which can have rounded ends, is usually arranged in the grinding drum. The rod is moved to a fro in the grinding drum by alternating electromagnetic fields, with the result that a grinding and homogenising procedure is initiated. The amount fed into the cryogenic mill is optional and can be adapted according to requirement.

During homogenisation in the cryogenic mill, the periods of cooling and grinding alternate. The periods can be of identical or different duration, depending on the polymer and the active constituent. The grinding drum is cooled by means of liquid nitrogen.

The polymers used in the homogenisation according to the invention should have a molecular weight average of from 5000 to 80000, preferably from 8000 to 40000 and especially from 9000 to 16000, and should be suitable for implants in terms of their compatibility. Such polymers are, for example, silicones, poly(dioxanones), poly(siloxanes), poly(glycolides) ethylene vinyl acetate copolymers, poly(L-lactides), poly(D,L-lactides-co-glycolides), poly(L-lactides-co-trimethylene carbonates) or poly(L-lactides-co-D,L-lactides). Preferred polymers are poly(L-lactides), poly(D,L-lactides), poly(D,L-lactides-co-glycosides) or poly(L-lactides-co-D,L-lactides).

The active constituent introduced in the homogenisation procedure can be, for example, a representative from the active ingredient group of the anabolic steroids, androgens, anti-androgens, gestagens, oestrogens, progestagens, anterior pituitary hormones, posterior pituitary hormones, hypothalamus hormones, prostaglandins, immunostimulating substances, anti-arrhythmics, analgesics, anti-rheumatics, anti-diabetics, osteoporotics, lipid-lowering agents, cytostatics, opiate antagonists and/or anti-anaemics.

There may be used as active constituent one or more representatives from the group of the anabolic steroids, for example nandrolone, clostebol, metenolone and/or derivatives thereof and/or pharmaceutically acceptable salts thereof.

There may be used as active constituent one or more representatives from the group of the androgens and synthetic analogues thereof, for example testosterone, mesterolone and/or derivatives thereof and/or pharmaceutically acceptable salts thereof.

There may be used as active constituent one or more representatives from the group of the anti-androgens, for example cyproterone, chlormadinone, mestranol, dienogest and/or derivatives thereof and/or pharmaceutically acceptable salts thereof.

There may be used as active constituent one or more representatives from the group of the gestagens and synthetic analogues thereof, for example medroxyprogesterone, dydrogesterone, norethisterone, levonorgestrel, lynestrenol, hydroxyprogesterone, medrogestone, progesterone, norgestimate, gestodene and/or derivatives thereof and/or pharmaceutically acceptable salts thereof.

There may be used as active constituent one or more representatives from the group of the oestrogens and synthetic analogues thereof, for example oestradiol, oestriol, ethynyl oestradiol, prasterone and/or derivatives thereof and/or pharmaceutically acceptable salts thereof.

There may be used as active constituent one or more representatives from the group of the progestagens and synthetic analogues thereof, for example desogestrel, etonogestrel and/or derivatives thereof and/or pharmaceutically acceptable salts thereof.

There may be used as active constituent one or more representatives from the group of the anterior pituitary hormones and synthetic analogues thereof, for example tetracosactide, chorionic gonadotrophin, urofollitrophin, somatropin, follitrophin, urogonadotrophin, menotrophin and/or derivatives thereof and/or pharmaceutically acceptable salts thereof.

There may be used as active constituent one or more representatives from the group of the posterior pituitary hormones and synthetic analogues thereof, for example desmopressin, terlipressin, oxytocin, argipressin and/or derivatives thereof and/or pharmaceutically acceptable salts thereof.

There may be used as active constituent one or more representatives from the group of the hypothalamus hormones (LH-releasing hormone) and synthetic analogues thereof, for example cetrorelix, corticorelin, triptorelin, leuprorelin, gonadorelin, ganirelix, buserelin, nafarelin, goserelin, somatostatin, octreotide and/or derivatives thereof and/or pharmaceutically acceptable salts thereof, especially leuprorelin acetate or goserelin acetate.

There may be used as active constituent one or more representatives from the group of the prostaglandins and synthetic analogues thereof, for example alprostadil, dinoprostone, dinoprost and/or derivatives thereof and/or pharmaceutically acceptable salts thereof.

There may be used as active constituent one or more representatives from the group of the immunostimulating substances and synthetic analogues thereof, for example interferons (α-, β-, γ-type), interleukins (I, II, III, VI, XI etc.), GM-CSF (milodistim, molgrodostim, sargrodostim), M-CSF, G-CSF (filgrastim, lenograstim), acemannan, ancestim, arbekacin, forfenimex, glycopin, imiquimod, imupedon, leridistim, methisoprinol, murabutide, pidotimod, romurtide, roquinimex, thymalfasin, thymocartin, thymoctonan, thymopentin, ubenimex.

There may be used as active constituent one or more representatives from the group of the anti-arrhythmics, for example adenosine, orciprenaline, aprindine, amiodarone, verapamil, motoprolol, esmolol, quinidine, sotalol, digoxin, β-acetyldigoxin, diltiazem, lidocaine, mexiletine, prajmalium, phenytoin, gallopamil, propafenone, detajmium, flecainide, atenolol, oxprenolol and/or derivatives thereof and/or pharmaceutically acceptable salts thereof.

There may be used as active constituent one or more representatives from the group of the analgesics/anti-rheumatics, for example morphine, pethidine, fentanyl, pentazocine, methadone, levacetylmethadol, buprenorphine, nefopam, trodadol, dextropropoxyphene, flupirtine, meptazinol, nalbuphine, tilidine, phenazone, metamizole, propyphenazone, paracetamol, phenylbutazone, mofebutazone, kebuzone, acemetacin, ibuprofen, naproxen, diclofenac, ketoprofen, indometacin, lonazolac, aceclofenac, mefenamic acid, etofenamate, tiaprofenic acid, azapropazone, lornoxicam, meloxicam, piroxicam, tenoxicam, penicillamine, chloroquine, methotrexate, auranofin, sodium aurothiomalate, oxaceprol, leflunomide, sulphasalazine, celecoxib, rofecoxib, etanercept, sitosterine, hyarulonic acid, flufenamic acid, felbinac, camphor, propyl nicotinate, levomenthol, benzyl nicotinate and/or derivatives thereof and/or pharmaceutically acceptable salts thereof.

There may be used as active constituent one or more representatives from the group of the anti-diabetics and synthetic analogues thereof, for example insulin, miglitol, metformin, phenformin, buformin, glibenclamide, tolbutamide, glimepiride, gliclazide, glibornuride, gliquidone, glisoxepide, pioglitazone, rosiglitazone, repaglinide and/or derivatives thereof and/or pharmaceutically acceptable salts thereof.

There may be used as active constituent one or more representatives from the group of the osteoporotics, for example sodium risedronate, disodium pamidronate, sodium ibandronate, sodium metidronate, disodium clodronate, sodium alendronate, disodium tiludronate, sodium fluoride, sodium fluorophosphate and/or derivatives thereof, dihydrotachysterol, calcitonin and/or derivatives thereof and/or pharmaceutically acceptable salts thereof.

There may be used as active constituent one or more representatives from the group of the lipid-lowering agents, for example fluvastatin, simvastatin, cerivastatin, pravastatin, lovastatin, atorvastatin, colestipol, cholestyrodine, xantinol nicotinate, dextrothyroxin, inositol nicotinate, acipimox, sitosterine, benzafibrate, fenofibrate, clofibrate, etofyllin clofibrate, etofibrate, gemfibrozil and/or derivatives thereof and/or pharmaceutically acceptable salts thereof.

There may be used as active constituent one or more representatives from the group of the cytostatics, for example aclarubicin, nimustine, doxorubicin, cytarabine, melphalan, mitomycin, bleomycin, carmustine, lomustine, vinblastine, estramustine cyclophosphamide, daunarubicin, etoposide, epirubicin, fludarabine, fluorouracil, gemcitabine, ifosamide, trofosfamide, chlorambucil, dactinomycin, busulfan, procarbazine, mitoxantrone, bendamustine paclitaxel, docetaxel, temozolomide, teniposide, cisplatin, camptothecin, idarubicin, vinca alkaloids and/or derivatives thereof and/or pharmaceutically acceptable salts thereof.

There may be used as active constituent one or more representatives from the group of the opiate antagonists, for example naltrexone, naloxone and/or derivatives thereof and/or pharmaceutically acceptable salts thereof.

There may be used as active constituent one or more representatives from the group of the anti-anaemics, for example erythropoietin alpha and/or erythropoietin beta.

There may also be used as active constituent growth hormones, endorphins, tumour necrosis factor and derivatives thereof.

It is also possible to use insulin as active constituent.

Pharmaceutically acceptable salts of the mentioned active constituents are to be understood as being, inter alia, acid addition salts. Such salts can be obtained by the reaction of the active constituent in its free form with pharmaceutically acceptable acids. The pharmaceutically acceptable acids may be inorganic acids (for example hydrochloric acid, hydrobromic acid, sulphuric acid, nitric acid, phosphoric acid) or organic acids (for example acetic acid, propionic acid, hydroxyacetic acid, lactic acid, pyruvic acid, oxalic acid, maleic acid, malonic acid, succinic acid, fumaric acid, malic acid, tartaric acid, citric acid, methanesulphonic acid, ethanesulphonic acid, benzenesulphonic acid, p-toluene-sulphonic acid, cyclohexanesulphamic acid, salicylic acid, p-aminosalicylic acid and pamoic acid).

Also designated as acid addition salts are solvates with the active ingredient. Such solvates are, for example, hydrates or alcoholates.

As possible pharmaceutically acceptable salts of the mentioned active constituents there also come into consideration alkali metal and/or alkaline earth metal salts and also the ammonium salt, such as, for example, the potassium, sodium, lithium, calcium, magnesium or ammonium salt.

The ratio of polymer(s) to active constituent is so selected that the content of active constituent(s) is from 5 to 50% by weight, based on the weight of the homogenisate.

The invention is illustrated in further detail by the following Examples, but without the scope of the invention being limited thereby.

EXAMPLE 1

1.5 g of leuprorelin acetate and 4.5 g of poly(D,L-lactide) (R202H) are weighed out and introduced into the polycarbonate grinding drum of a cryogenic mill (SPEX CertiPrep 6800 Freezer/Mill). The mixture is precooled in the grinding drum for 15 minutes using liquid nitrogen. Also arranged in the grinding drum is a grinding rod having substantially rounded edges. First of all, cooling is carried out for 2 minutes, and then grinding is carried out for 2 minutes at 10 Hz. That sequence is repeated. The grinding vessel is then thawed in the sealed state. This is followed by extrusion, cutting and weighing. The implants are packaged, and introduced into prefabricated syringes.

EXAMPLE 2

1.5 g of leuprorelin acetate and 4.5 g of poly(D,L-lactide-co-glycolide) are weighed out and introduced into the polycarbonate grinding drum of a cryogenic mill (SPEX CertiPrep 6800 Freezer/Mill). The mixture is precooled in the grinding drum for 15 minutes using liquid nitrogen. Also arranged in the grinding drum is a grinding rod having substantially rounded edges. First of all, cooling is carried out for 2 minutes, and then grinding is carried out for 2 minutes at 12 Hz. That sequence is repeated. The grinding vessel is then thawed in the sealed state. This is followed by extrusion.

EXAMPLE 3

1.5 g of leuprorelin acetate and 4.5 g of poly(D,L-lactide-co-glycolide) are weighed out and introduced into the polycarbonate grinding drum of a cryogenic mill (SPEX CertiPrep 6800 Freezer/Mill). The mixture is precooled in the grinding drum for 15 minutes using liquid nitrogen. Also arranged in the grinding drum is a grinding rod having substantially rounded edges. First of all, cooling is carried out for 2 minutes, and then grinding is carried out for 2 minutes at 8 Hz. That sequence is repeated. The grinding vessel is then thawed in the sealed state. This is followed by extrusion.

EXAMPLE 4

1.5 g of leuprorelin acetate and 4.5 g of poly(D,L-lactide) are weighed out and introduced into the polycarbonate grinding drum of a cryogenic mill (SPEX CertiPrep 6800 Freezer/Mill). The mixture is precooled in the grinding drum for 15 minutes using liquid nitrogen. Also arranged in the grinding drum is a grinding rod having substantially rounded edges. First of all, cooling is carried out for 2 minutes, and then grinding is carried out for 2 minutes at 12 Hz. That sequence is repeated. The grinding vessel is then thawed in the sealed state. This is followed by extrusion.

EXAMPLE 5

1.5 g of leuprorelin acetate and 4.5 g of poly(D,L-lactide) are weighed out and introduced into the polycarbonate grinding drum of a cryogenic mill (SPEX CertiPrep 6800 Freezer/Mill). The mixture is precooled in the grinding drum for 15 minutes using liquid nitrogen. Also arranged in the grinding drum is a grinding rod having substantially rounded edges. First of all, cooling is carried out for 2 minutes, and then grinding is carried out for 2 minutes at 10 Hz. That sequence is repeated four times. The grinding vessel is then thawed in the sealed state. This is followed by extrusion.

EXAMPLE 6

1.5 g of goserelin acetate and 4.5 g of poly(D,L-lactide) are weighed out and introduced into the polycarbonate grinding drum of a cryogenic mill (SPEX CertiPrep 6800 Freezer/Mill). The mixture is precooled in the grinding drum for 15 minutes using liquid nitrogen. Also arranged in the grinding drum is a grinding rod having substantially rounded edges. First of all, cooling is carried out for 2 minutes, and then grinding is carried out for 2 minutes at 10 Hz. That sequence is repeated five times. The grinding vessel is then thawed in the sealed state. This is followed by extrusion.

EXAMPLE 7

3.0 g of leuprorelin acetate and 9.0 g of poly(D,L-lactide) are weighed out and introduced into the polycarbonate grinding drum of a cryogenic mill (SPEX CertiPrep 6800 Freezer/Mill). The mixture is precooled in the grinding drum for 15 minutes using liquid nitrogen. Also arranged in the grinding drum is a grinding rod having substantially rounded edges. First of all, cooling is carried out for 2 minutes, and then grinding is carried out for 2 minutes at 10 Hz. That sequence is repeated three times. The grinding vessel is then thawed in the sealed state. This is followed by extrusion.

EXAMPLE 8

6.0 g of leuprorelin acetate and 18.0 g of poly(D,L-lactide) are weighed out and introduced into the polycarbonate grinding drum of a cryogenic mill (SPEX CertiPrep 6800 Freezer/Mill). The mixture is precooled in the grinding drum for 15 minutes using liquid nitrogen. Also arranged in the grinding drum is a grinding rod having substantially rounded edges. First of all, cooling is carried out for 2 minutes, and then grinding is carried out for 2 minutes at 10 Hz. That sequence is repeated three times. The grinding vessel is then thawed in the sealed state. This is followed by extrusion.

The invention claimed is:
1. Solvent-free method of producing implants, comprising the steps of:
    (a) cooling together raw materials comprising at least one pharmaceutically active constituent and at least one polymer compatible therewith, said materials in the form of powders or granules, in a cryogenic mill to a temperature applied in cryogenic technology;
    (b) completely homogenizing the raw materials together in said mill at a temperature below the glass transition temperature of the at least one polymer; and
    (c) thereafter bringing the homogenized raw materials to room temperature and obtaining the resulting homogenizate
    wherein said steps (a) to (c) are carried out in the absence of solvent; and
    (d) further processing the homogenizate obtained to form an implant;
    wherein the polymer is selected from one or more in the group consisting of poly(L-lactides), poly(D,L-lactides), poly(D,L-lactides-co-glycolides), and poly(L-lactides-co-D,L-lactides.
2. Method according to claim 1, comprising carrying out said cooling step to the temperature of dry ice or of a liquid gas.
3. Method according to claim 1, comprising carrying out said cooling step to the operating temperature of a cryogenic mill.
4. Method according to claim 1, comprising carrying out the process steps of cooling and homogenizing repeatedly in succession.
5. Method according to claim 1, comprising carrying out said homogenizing step mechanically.
6. Method according to claim 5, comprising carrying out said homogenizing step by grinding.
7. Method according to claim 1, comprising extruding and dividing the homogenizate into portions to form implant(s).
8. Method according to claim 2, comprising carrying out said cooling step to the temperature of liquid nitrogen.
9. Method according to claim 6, comprising carrying out grinding with the aid of a cryogenic mill.
10. An implant comprising the homogenizate of claim 1.
11. Method according to claim 1, wherein the at least one polymer compatible with the at least one pharmaceutically active constituent has a weight average molecular weight in a range of 5,000 to 80,000 Dalton.

12. Method according to claim 11, wherein the at least one pharmaceutically active constituent is selected from the group consisting of hypothalamus hormones and synthetic analogues thereof.

13. Method according to claim 11, wherein the at least one pharmaceutically active constituent is selected from the group consisting of cetrorelix, corticorelin, triptorelin, leuprorelin, gonadorelin, ganirelix, buserelin, nafarelin, goserelin and/or derivatives thereof and/or pharmaceutically acceptable salts thereof.

14. Method according to claim 1, wherein the at least one pharmaceutically active constituent is selected from the group consisting of hypothalamus hormones and synthetic analogues thereof.

15. Method according to claim 1, wherein the at least one pharmaceutically active constituent is selected from the group consisting of cetrorelix, corticorelin, triptorelin, leuprorelin, gonadorelin, ganirelix, buserelin, nafarelin, goserelin and/or derivatives thereof and/or pharmaceutically acceptable salts thereof.

16. Method according to claim 1, wherein the at least one pharmaceutically active constituent is selected from the group consisting of LH-releasing hormone and synthetic analogues thereof.

17. Solvent-free method of producing implants, comprising the steps of:
(a) feeding raw materials comprising at least one pharmaceutically active constituent and at least one polymer compatible therewith, said materials in the form of powders or granules, into a cryogenic mill;
(b) cooling the combination of raw materials in the cryogenic mill to a temperature applied in cryogenic technology;
(c) completely homogenizing the raw materials together in said mill at a temperature below the glass transition temperature of the at least one polymer; and
(d) thereafter bringing the homogenized raw materials to room temperature and obtaining the resulting homogenizate
wherein said steps (a) to (d) are carried out in the absence of solvent; and
(e) further processing the homogenize obtained to form an implant;
wherein the at least one polymer compatible with the at least one pharmaceutically active constituent is selected from the group consisting of poly(L-lactides), poly(D, Llactides), poly(D,L-lactides-co-glycolides), poly(L-lactides-co-D,L-lactides), and combinations thereof.

18. Method according to claim 11, wherein the at least one pharmaceutically active constituent is selected from the group consisting of LH-releasing hormone and synthetic analogues thereof.

19. Solvent-free method of producing implants, comprising the steps of:
(a) feeding raw materials comprising at least one pharmaceutically active constituent and at least one polymer compatible therewith, said materials in the form of powders or granules, into a cryogenic mill;
(b) cooling the combination of raw materials in the cryogenic mill to a temperature applied in cryogenic technology;
(c) completely homogenizing the raw materials together by grinding in said mill at a temperature below the glass transition temperature of the at least one polymer; and
(d) thereafter bringing the homogenized raw materials to room temperature and obtaining the resulting homogenizate
wherein said steps (a) to (d) are carried out in the absence of solvent; and
(e) further processing the homogenizate obtained to form an implant;
wherein the at least one polymer compatible with the at least one pharmaceutically active constituent is selected from the group consisting of poly(L-lactides), poly(D, Llactides), poly(D,L-lactides-co-glycolides), poly(L-lactides-co-D,L-lactides), and combinations thereof.

20. Method according to claim 16, wherein the ratio of the polymer(s) to active constituent(s) is selected such that the content of the pharmaceutically active constituent(s) is from 5% to 50% by weight, based on the weight of the homogenisate.

21. Method according to claim 19, wherein the raw materials are cooled together and subsequently homogenized.

* * * * *